US012678158B2

(12) United States Patent
Bushko et al.

(10) Patent No.: US 12,678,158 B2
(45) Date of Patent: Jul. 14, 2026

(54) BONE STAPLE SYSTEM

(71) Applicant: Concise Engineering, Inc., Clearwater, FL (US)

(72) Inventors: Justin Bushko, Clearwater, FL (US); Giuseppe Lombardo, Trinity, FL (US); Daniel Riveros, Redington Shores, FL (US)

(73) Assignee: Concise Engineering, Inc., Clearwater, FL (US)

( * ) Notice: Subject to any disclaimer, the term of this patent is extended or adjusted under 35 U.S.C. 154(b) by 303 days.

(21) Appl. No.: 18/131,856

(22) Filed: Apr. 6, 2023

(65) Prior Publication Data

US 2023/0346369 A1 Nov. 2, 2023

Related U.S. Application Data

(60) Provisional application No. 63/337,578, filed on May 2, 2022.

(51) Int. Cl.
| | |
|---|---|
| *A61B 17/064* | (2006.01) |
| *A61B 17/00* | (2006.01) |
| *A61B 17/068* | (2006.01) |
| *A61B 17/072* | (2006.01) |
| *A61B 17/10* | (2006.01) |
| *A61B 17/56* | (2006.01) |

(52) U.S. Cl.
CPC .......... *A61B 17/0642* (2013.01); *A61B 17/10* (2013.01); *A61B 2017/0046* (2013.01); *A61B 2017/00477* (2013.01); *A61B 17/064* (2013.01); *A61B 17/0644* (2013.01); *A61B*

*2017/0645* (2013.01); *A61B 2017/0646* (2013.01); *A61B 17/068* (2013.01); *A61B 17/0682* (2013.01); *A61B 2017/07214* (2013.01); *A61B 2017/564* (2013.01)

(58) Field of Classification Search
CPC ..... A61B 17/0642; A61B 17/10; A61B 17/17; A61B 17/064; A61B 17/0644; A61B 17/068; A61B 17/0682; A61B 2017/0046; A61B 2017/00477; A61B 2017/0645; A61B 2017/564; A61B 2017/0646; A61B 2017/07214
USPC ... 606/75, 300, 78, 86 R, 87, 907, 908, 911, 606/105
See application file for complete search history.

(56) References Cited

U.S. PATENT DOCUMENTS

| | | | |
|---|---|---|---|
| 5,209,756 | A | 5/1993 | Seedhom et al. |
| D484,032 | S | 12/2003 | Del Re |
| D625,417 | S | 10/2010 | Fox et al. |
| 8,393,517 | B2 | 3/2013 | Milo |
| 8,584,853 | B2 | 11/2013 | Knight et al. |
| 8,596,514 | B2 | 12/2013 | Miller et al. |
| D701,307 | S | 3/2014 | Protopsaltis et al. |
| 8,679,123 | B2 | 3/2014 | Kinmon et al. |
| D707,357 | S | 6/2014 | Cheney et al. |
| D723,688 | S | 3/2015 | Knight |
| 9,095,338 | B2 | 8/2015 | Taylor et al. |
| D756,513 | S | 5/2016 | Cheney |
| 9,402,624 | B1 | 8/2016 | Scott et al. |
| 9,486,212 | B2 | 11/2016 | Miller et al. |

(Continued)

*Primary Examiner* — Marcela I. Shirsat
(74) *Attorney, Agent, or Firm* — Offit Kurman; Gregory A. Grissett

(57) ABSTRACT

A bone staple system configured to secure one or more bone segments and related methods is provided.

29 Claims, 14 Drawing Sheets

(56)  References Cited

U.S. PATENT DOCUMENTS

| | | | |
|---|---|---|---|
| D777,329 S | 1/2017 | Montoya et al. | |
| D780,311 S | 2/2017 | Cheney et al. | |
| 10,188,388 B2 | 1/2019 | Handie | |
| D870,284 S | 12/2019 | Hollis et al. | |
| D886,299 S | 6/2020 | Cundiff et al. | |
| D895,113 S | 9/2020 | Blair et al. | |
| 11,006,949 B2 | 5/2021 | Daniel | |
| D957,636 S | 7/2022 | Blair et al. | |
| D1,017,038 S | 3/2024 | Bushko et al. | |
| 2004/0138705 A1 | 7/2004 | Heino et al. | |
| 2008/0167666 A1 | 7/2008 | Fiere et al. | |
| 2012/0085809 A1* | 4/2012 | Milo | A61B 17/0644 |
| | | | 227/181.1 |
| 2013/0026207 A1* | 1/2013 | Fox | A61B 17/0642 |
| | | | 227/176.1 |
| 2013/0231667 A1 | 9/2013 | Taylor et al. | |
| 2014/0014553 A1* | 1/2014 | Knight | B65D 85/00 |
| | | | 206/570 |
| 2014/0097228 A1 | 4/2014 | Taylor et al. | |
| 2015/0083774 A1* | 3/2015 | Measamer | A61B 17/1155 |
| | | | 227/175.1 |
| 2015/0133940 A1 | 5/2015 | Palmer et al. | |
| 2016/0066907 A1 | 3/2016 | Cheney et al. | |
| 2016/0074037 A1 | 3/2016 | Cheney et al. | |
| 2016/0235460 A1* | 8/2016 | Wahl | A61B 17/064 |
| 2017/0196678 A1 | 7/2017 | Park et al. | |
| 2017/0202552 A1 | 7/2017 | Coleman et al. | |
| 2017/0231625 A1 | 8/2017 | Handie | |
| 2017/0252036 A1 | 9/2017 | Palmer et al. | |
| 2019/0117219 A1 | 4/2019 | Ritz et al. | |
| 2019/0150921 A1 | 5/2019 | Fonte et al. | |
| 2021/0068822 A1 | 3/2021 | Wahl | |
| 2021/0128145 A1 | 5/2021 | Taylor et al. | |
| 2021/0228206 A1 | 7/2021 | Cheney et al. | |
| 2021/0386422 A1 | 12/2021 | Maclure et al. | |
| 2023/0346369 A1 | 11/2023 | Bushko et al. | |

* cited by examiner

120D

120E

120H

280

290

200

300

310

β

304

200

310

300

α

304

302

241

286

286

BONE STAPLE SYSTEM

CROSS-REFERENCE TO RELATED APPLICATIONS

The present application claims the benefit of and priority to U.S. Provisional Application Ser. No. 63/337,578, filed May 2, 2022, the entire contents of which are incorporated by reference into the present application.

TECHNICAL FIELD

The present disclosure relates generally to a bone staple system for securing bone segments and related methods.

BACKGROUND

A common procedure for handling healing of broken bones or fractures is the use of bone staples for securing one or more adjacent bone structures to facilitate healing. In the treatment of bone fractures, conventional bone staple devices utilize compression to stabilize and immobilize adjacent bone structures to promote healing. Some bone staple systems stabilize adjacent bone structures but result in improper spacing which prevents the establishment of desired compression forces between the adjacent structures for optimal healing outcomes. Such systems often require multiple components requiring customization depending on the type of bone, patient, or location of the bone fractures in the body of a patient. This results in increased costs, less desirable treatment outcomes, and multiple procedures to ensure that a bone staple is properly placed.

SUMMARY

There is a need for a bone staple system capable of providing compressive forces to adjacent bone structures that addresses the aforementioned problems of conventional bone staple systems including precisely pre-drilling holes in adjacent bone structures and delivering a staple in a manner that removes guesswork by a user and does not require multiple components or devices to achieve optimal healing outcomes.

An embodiment of the present disclosure includes a bone staple system. The bone staple system includes an inserter assembly configured to deliver a staple into a fixation site. The inserter assembly includes a housing, an end effector, a fulcrum, a cam assembly, and an actuator. The housing includes a leading end and a trailing end opposite the leading end along a longitudinal axis. The end effector is moveable along the longitudinal axis relative to the housing between a first position and a second position. The fulcrum is fixed to the housing and engages the end effector, wherein the fulcrum and the end effector are configured to hold the staple. The cam assembly is coupled to the end effector and the actuator is coupled to the cam assembly. Actuation of the actuator moves the end effector between the first position and the second position.

Another embodiment of the disclosure is an inserter assembly configured to deliver a staple into a fixation site. The inserter assembly includes a housing, an end effector, a pin, a cam assembly, and an actuator. The housing includes a leading end and a trailing end opposite the leading end along a longitudinal axis. The end effector is moveable along the longitudinal axis relative to the housing between a first position and a second position. The pin is fixed to the housing and engages the end effector, wherein the pin and the end effector are configured to secure the staple. The cam assembly is coupled to the end effector and the actuator is coupled to the cam assembly. Actuation of the actuator moves the end effector between the first position and the second position.

Another embodiment of the disclosure is a method for anchoring a staple to a fixation site of two or more bone segments. The method includes positioning a hub of an inserter assembly toward the fixation site, wherein the hub carries a staple having a pair of legs that are biased inwardly in a converging state. The method further includes advancing the hub that carries the staple having the pair of legs in a proximal direction toward a proximal end of the inserter assembly so that a bridge of the staple abuts a pin mounted to a distal end of the inserter assembly, thereby causing the pair of legs of the staple to bias outwardly from the converging state, where the pair of legs are biased toward each other, to an insertion state out of the converging state. The method further includes the steps of inserting the pair of legs into the two or more bone segments so that the bridge of the staple traverses the fixation site while the staple is in the insertion state, and advancing the hub in a distal direction that is opposite the proximal direction, thereby causing the pair of legs to converge inwardly toward the converging state in order to anchor the staple at the fixation site.

Another embodiment of the disclosure is a method for anchoring a staple to a fixation site of two or more bone segments. The method includes positioning an end effector of an inserter assembly in alignment with the fixation site, wherein the end effector carries a staple having a bridge and a pair of legs in a converging state where the legs converge inwardly toward each other. The method further includes advancing the end effector in a proximal direction toward a proximal end of a housing of the inserter assembly so that the bridge of the staple abuts a pin mounted within the housing, so as to apply a force to the bridge that biases the pair of legs of the staple outwardly into an insertion state. The method further includes the steps of implanting the pair of legs, when in the insertion state, into the fixation site, and retracting the end effector in a distal direction that is opposite the proximal direction, so as to cause the pair of legs to converge inwardly to secure the staple at the fixation site.

BRIEF DESCRIPTION OF THE DRAWINGS

The foregoing summary, as well as the following detailed description of exemplary embodiments of the present application, are better understood when read in conjunction with the appended drawings. For the purposes of illustrating the present application, there is shown in the drawings, exemplary embodiments of the disclosure. It should be understood, however, that the application is not limited to the precise arrangements and instrumentalities shown. In the drawings.

DETAILED DESCRIPTION OF ILLUSTRATIVE EMBODIMENTS

Figure 1:
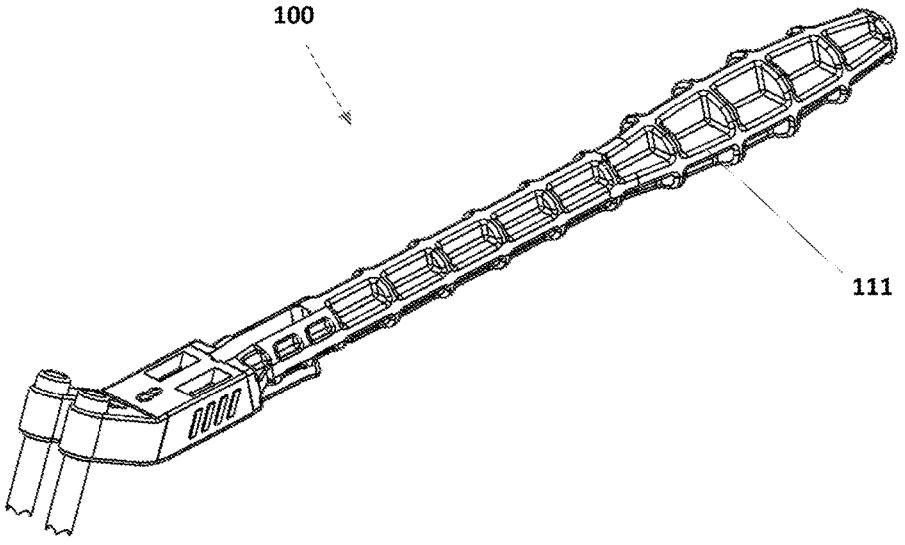
FIG. 1 is a perspective view of a drill guide assembly of a bone staple system in accordance with an exemplary embodiment of the present disclosure.

Bone staple systems as described are configured for interphalangeal joint fractures. While the embodiments described are configured for interphalangeal joint fractures, it is possible that the described embodiments could be configured for healing fractures of phalanges, metatarsals, cuneiform, or cuboid bones in the foot. In other embodiments, the bone staple systems may be configured for healing of bone segments of phalanges, metatarsals or other bones in the hand.

Referring to FIGS. 1-21, there is shown an exemplary embodiment of a bone staple system in accordance with the present disclosure. The bone staple system includes a drill guide assembly, inserter assembly 200, and one or more staples 300. Specifically, FIGS. 1-5 illustrate the drill guide assembly 100 of the bone staple system configured to guide one or more instruments for preparation of a fixation site for two adjacent bone segments and FIGS. 9-20 illustrate the inserter assembly 200. The inserter assembly 200 (FIGS. 9-20) is configured to deliver an implant, such as the staple 300 (FIG. 21), to a pair of holes drilled by the drill guide assembly 100 (FIGS. 1-5) at the fixation site.

Referring now to FIGS. 9-20, an inserter assembly 200 is shown that is configured to hold the staple 300 in position for implantation at the fixation site. The inserter assembly 200 includes a housing 220, end effector 230, fulcrum 270, cam assembly 240, and an actuator 210. As discussed below, the actuator 210 is configured to cause the end effector 230 to move between a first position, where legs of the staple are biased inwardly toward each other, and a second position, where the legs of the staple are biased outwardly with respect to each other. Additionally, the staple 300 can be held in position at least partially by the end effector 230 and fulcrum 270 when the end effector is in the second position.

Figure 9:
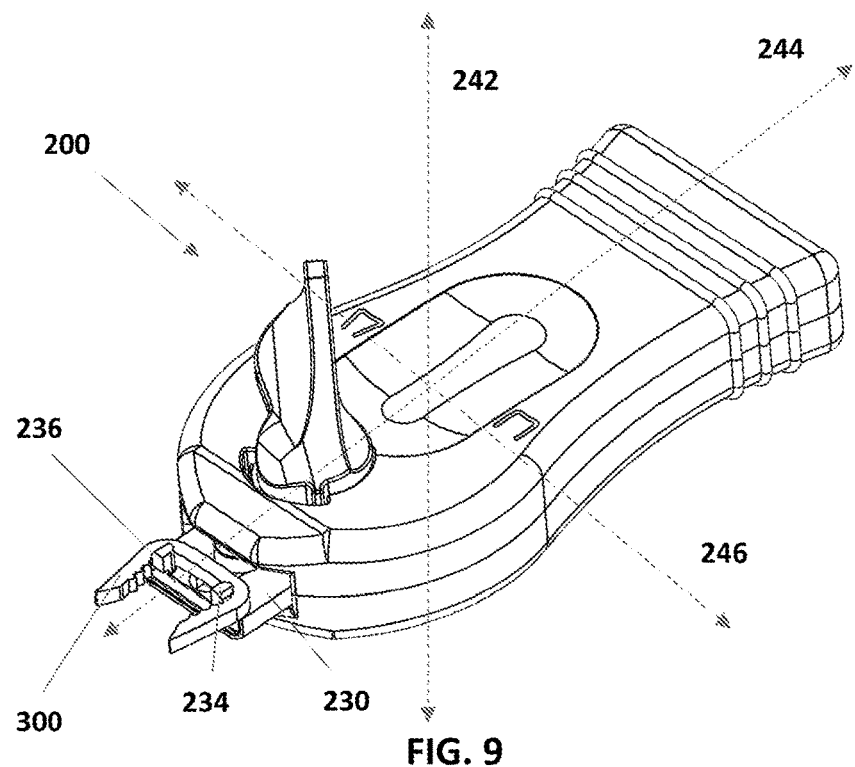
FIG. 9 is a perspective view of an inserter assembly of a bone staple system in accordance with an exemplary embodiment of the present disclosure.
Figure 10:
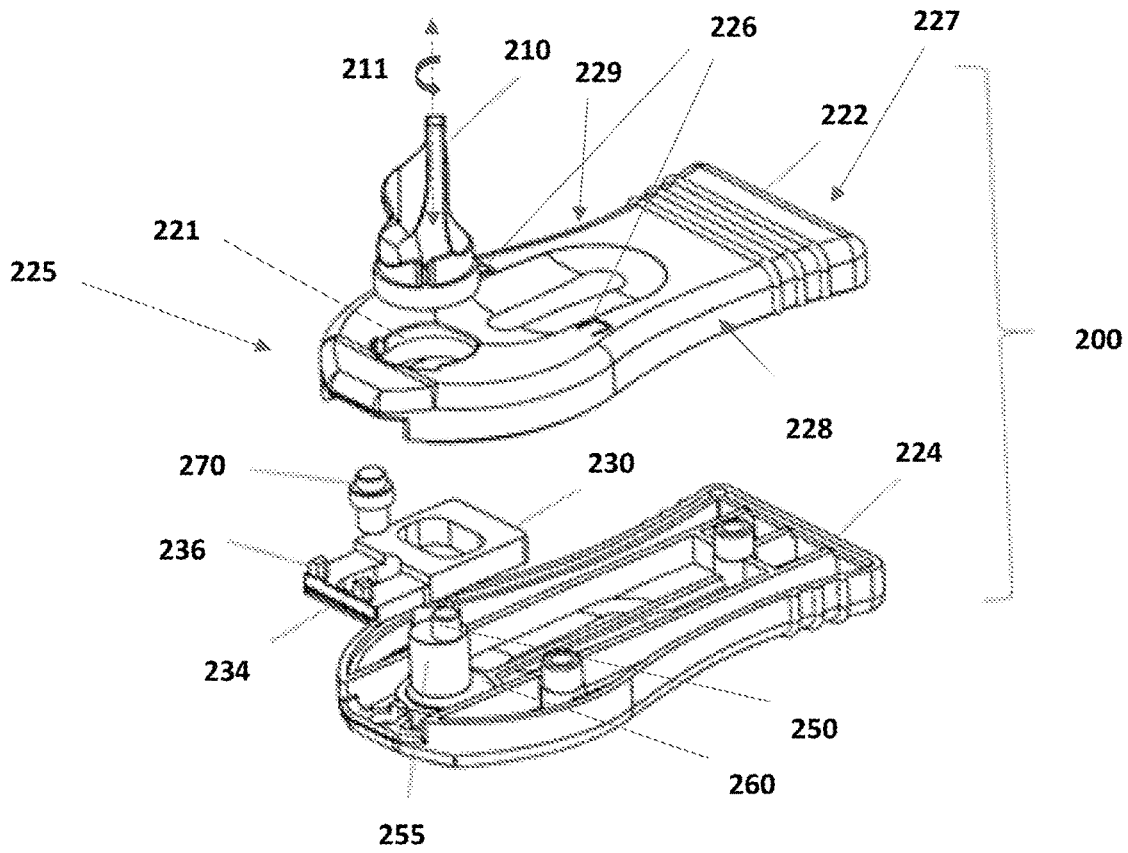
FIG. 10 is an exploded perspective view of the inserter assembly of FIG. 9.
Figures 13, 14:
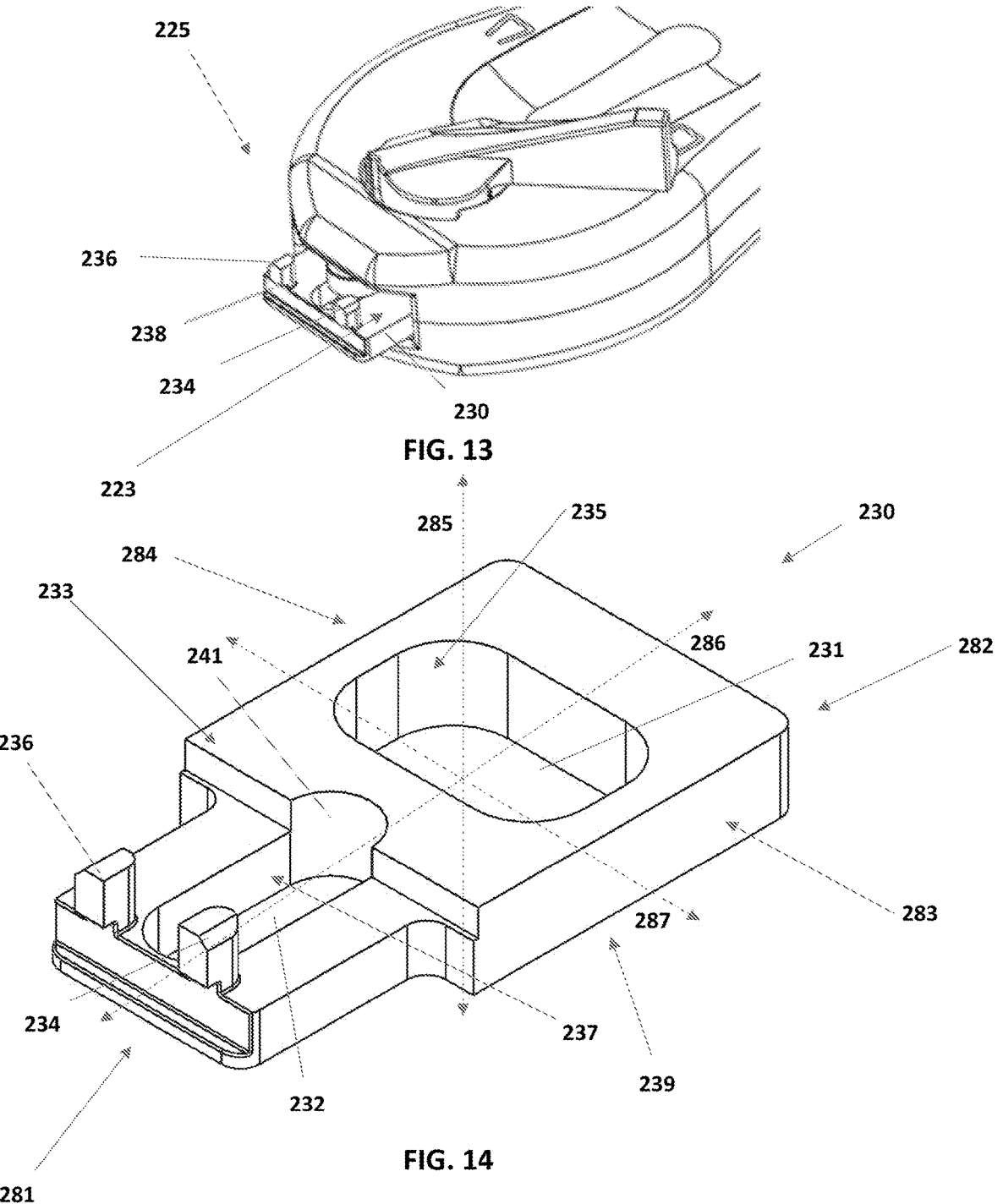
FIG. 13 is a partial perspective view of the inserter assembly of FIG. 9.
FIG. 14 is a perspective view of an end effector of the inserter assembly of FIG. 9.

As shown in FIGS. 9, 10 and 13, the housing 220 of the inserter assembly 200 includes a top 222, a bottom 224, a leading end 225, and a trailing end 227 opposite the leading end 225, and opposed sides 228, 229. The top 222 and bottom 224 are opposed to each other along a vertical axis 242, and the leading end 225 and trailing end 227 are opposed to each other along a longitudinal axis 244 that is perpendicular to and intersects the vertical axis 242. The opposed sides 228, 229 are spaced apart with respect to each other along a lateral axis 246 that is perpendicular to and intersects the vertical axis 242 and the longitudinal axis 244. In this disclosure, a proximal direction P is generally a direction from the leading end 225 toward the trailing end 227 and distal direction D is a direction generally from the trailing end 227 toward the leading end 225.

The top 222 and bottom 224 are complementary in shape and mount to one another. The housing 220 includes a through hole 221 extending from top 222 and an elongated window 223 (FIG. 13) at the leading end 225 of the housing 220. The elongated window 223 is configured to slidably receive a portion of the end effector 230 therethrough as the end effector 230 slidably transitions along the longitudinal axis 244 between the first position and the second position for biasing a staple 300. That is, a portion of the end effector 230 is generally positioned within the housing 220 when the inserter assembly 200 is assembled. It is to be understood that end effector 230 extends distally through the elongated window 223 of housing 220.

As further discussed below, the actuator 210 extends through the through hole 221 and is fixed to the cam assembly 240. In other words, the actuator 210 is coupled to the cam assembly 240 through the through hole 221 of the housing 220. The top 222 of the housing 220 may include indicia 226 for identifying the position of the actuator 210 and therefore the state of the staple 300. The actuator 210 is illustrated as a lever that is rotatable about a rotation axis 211 that generally is perpendicular to top 222 and bottom 224 of the housing. As further explained below, rotation of the actuator 210 about the rotation axis 211 causes the end effector to move between the first and second positions. The indicia 226, when used, can help a user identify the outer rotational limits of the actuator 210 to facilitate operation of the inserter assembly 200 by the user, e.g., surgeon. In accordance with an aspect, the actuator 210 actuates approximately 100 degrees about the rotation axis 211 when the end effector is moved from the first position to the second position.

Referring now to FIGS. 10-18, the end effector 230 is partially mounted within the housing 220. The end effector 230 extends between the top 222 and bottom 224 of the housing 220. That is, the end effector 230 is slidably mounted within an internal cavity of the housing 220 when moving between the first position and the second position. As further discussed below, in the first position (FIG. 11), the staple 300 is in a non-flexed state. In the second position (FIG. 12), the staple 300 is in a flexed state for insertion into the respective bone segments. In other words, the end effector 230 is configured to reciprocate between the first and second positions through the elongated window 223 of the housing 220 when the actuator 210 is actuated by the user.

Figure 15:
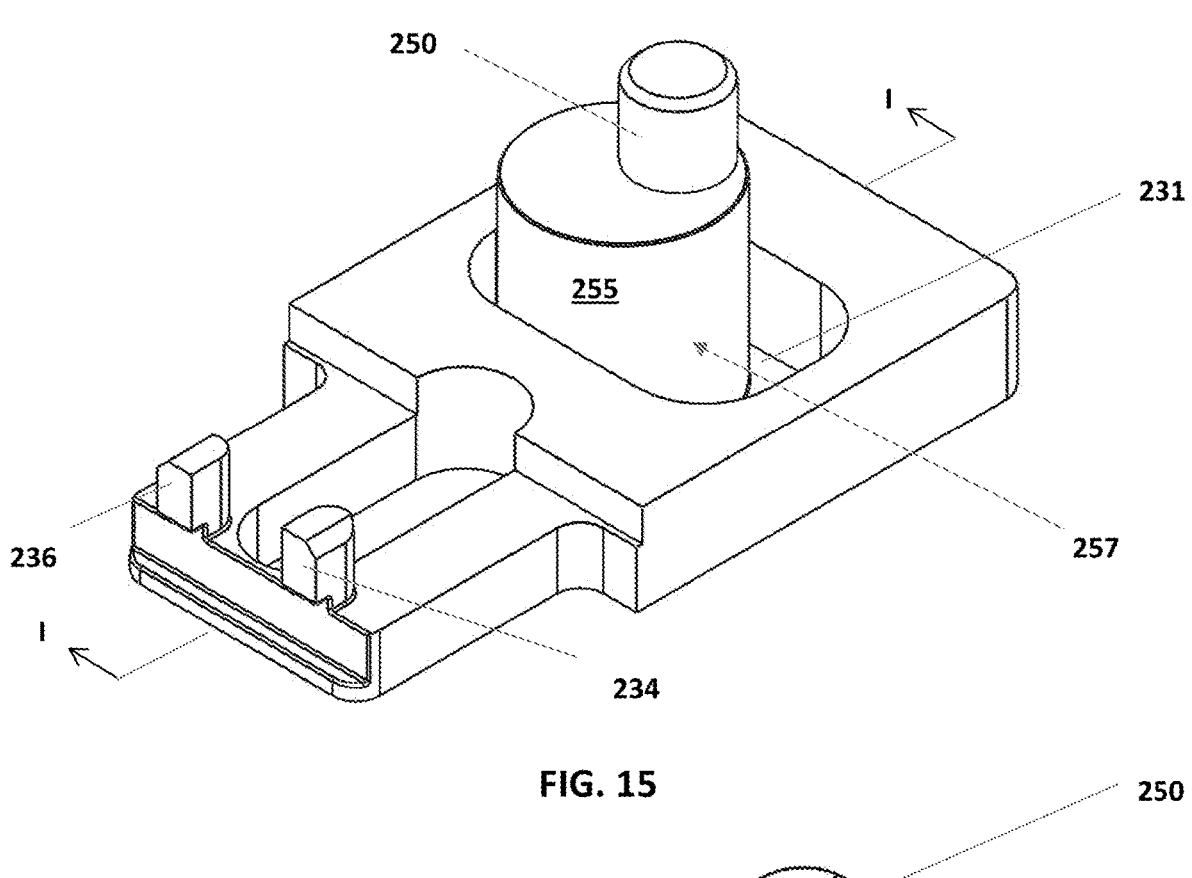
FIG. 15 is a perspective view of the end effector and cam assembly of the inserter assembly of FIG. 9.
Figure 16:
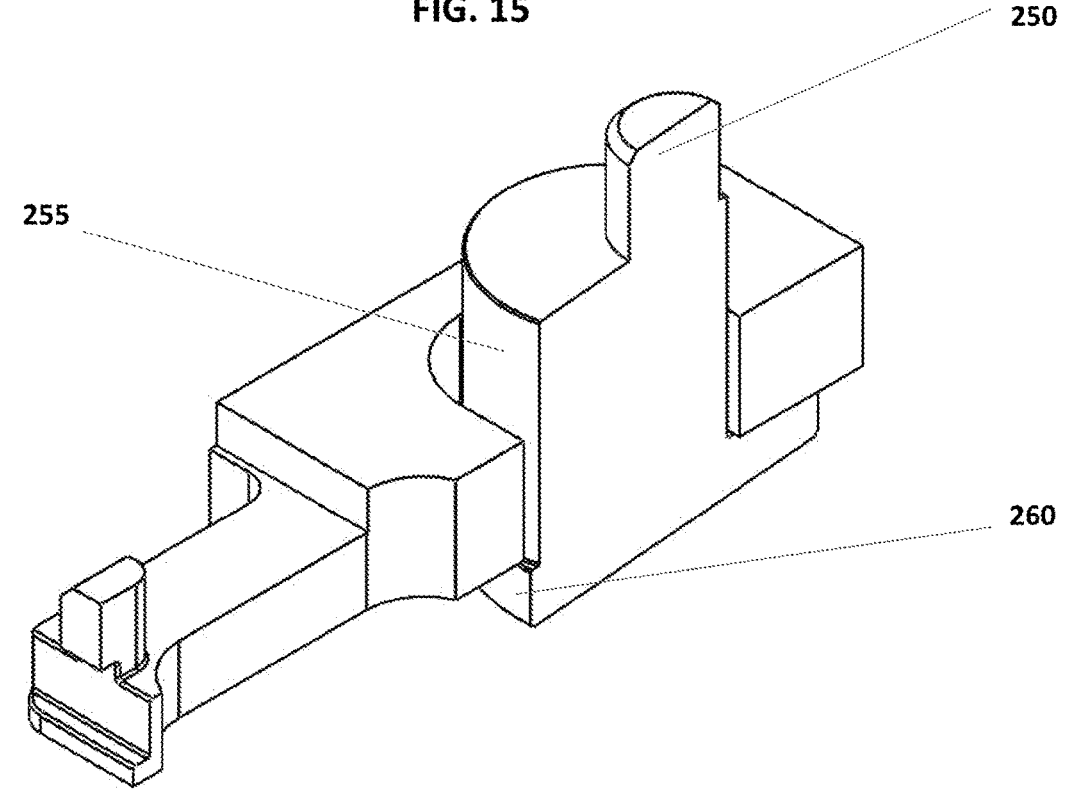
FIG. 16 is a partial side cross-sectional view of the end effector and cam assembly taken along line I-I in FIG. 15.

As shown in FIGS. 14-16, the end effector 230 is configured as a hub that includes a body having an upper surface 233, lower surface 239, an engagement end 281, and a rearward end 282 opposite the engagement end 281, and opposed sides 283, 284. The upper surface 233 and lower surface 239 are opposed to each other along a vertical axis 285, and the engagement end 281 and rearward end 282 are opposed to each other along a longitudinal axis 286 that is perpendicular to and intersects the vertical axis 285. The opposed sides 283, 284 are spaced apart with respect to each other along a lateral axis 287 that is perpendicular to and intersects the vertical axis 285 and the longitudinal axis 286.

As best shown in FIG. 14, the end effector 230 includes a first elongated slot 231 and a second elongated slot 232 spaced from the first elongated slot. The first elongated slot 231 is positioned about the rearward end 282 and extends through end effector 230 from the upper surface 233 to lower surface 239. The second elongated slot 232 is positioned about the engagement end 281 and extends through end effector 230 from the upper surface 233 to lower surface 239. The first elongated slot 231 includes a first inner perimeter 235. Similarly, the second elongated slot 232 includes a second inner perimeter 237.

In accordance with an aspect, the end effector 230 further includes a pair of projections 234, 236 about engagement end 281 for adjustably securing the staple 300 to the inserter assembly 200. The end effector 230 further includes a slotted area 238 about engagement end 281 for facilitating tamping the staple 300 into drilled holes in respective bone segments during operation of the bone staple system by a user.

As further discussed below, the first elongated slot 231 is configured to receive a portion of the cam assembly 240 therethrough. Similarly, the second elongated slot 232 is configured to receive the fulcrum 270 therethrough. When the end effector 230 is transitioning from the first position (FIG. 11) to the second position (FIG. 12), the cam assembly 240 slidably moves along the first inner perimeter 235 of the first elongated slot 231. Similarly, the fulcrum 270 translates along the second inner perimeter 237 of the second elongated slot 232 when the end effector 230 is transitioning from the first position to the second position. The respective inner perimeters 235, 237 are adapted to limit movement of the end effector 230 between the first position and second position by creating a limited travel path along which the cam assembly 240 and fulcrum 270 can respectively travel during operation.

As shown in FIGS. 9, 11, 12, 19 and 20, the projections 234, 236 provide a biasing force against an inner surface of the staple 300. In general, it is to be understood that the staple 300 can be secured to the inserter assembly 200 with a plurality of different mating features including, but not limited to, barbs, grooves, fasteners and the like.

Figure 17:
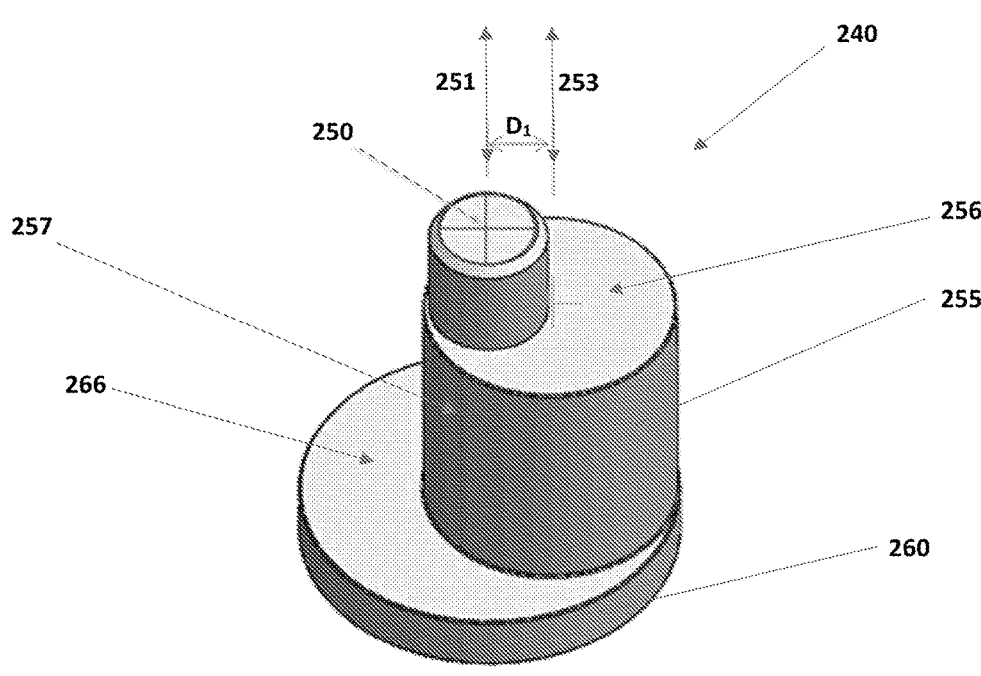
FIG. 17 is a perspective view of the cam assembly of the inserter assembly of FIG. 9.
Figure 18:
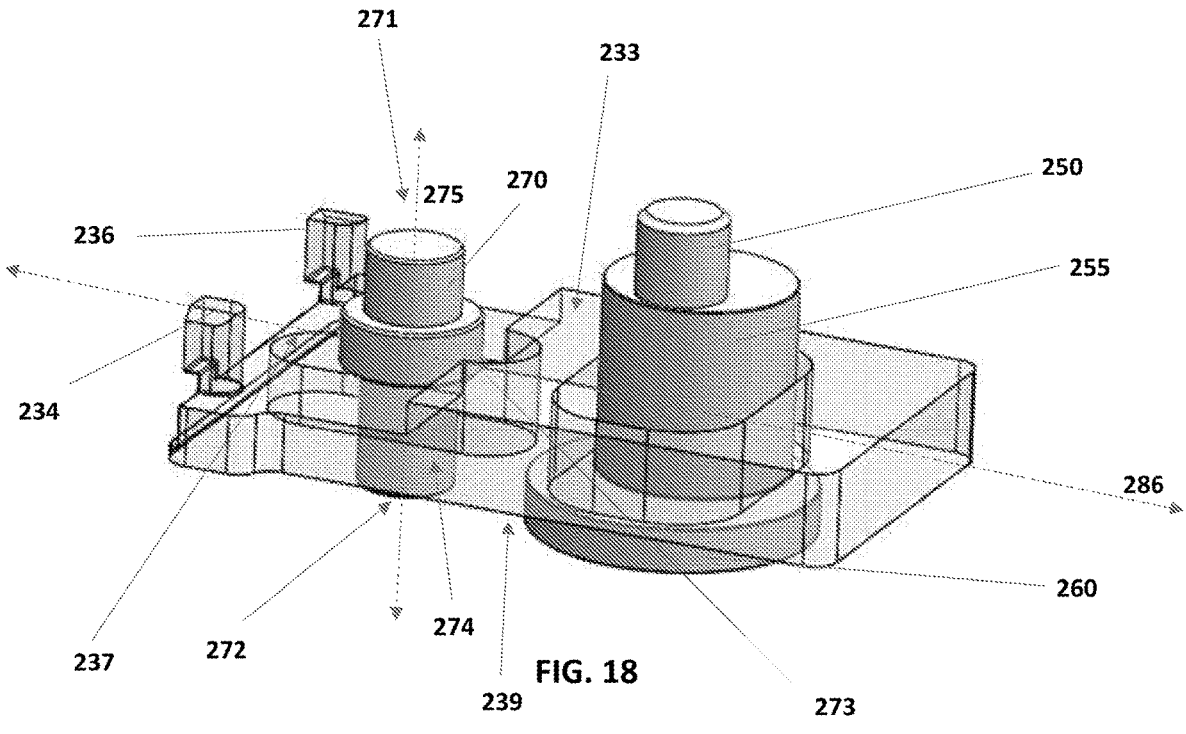
FIG. 18 is a partial perspective view of the inserter assembly of FIG. 9 with certain parts omitted and transparent for illustrative purposes.

Referring now to FIGS. 10 and 15-20, the cam assembly 240 includes an upper cam member 250, a central cam member 255 and a lower cam member 260. As shown in FIGS. 16-18, the upper cam member 250, central cam member 255, and lower cam member 260 are each fixedly connected to one another and configured as substantially annular members having a substantially circular cross-sectional shape. Specifically, the cross-sectional shape of the upper cam member is perpendicular to a first longitudinal axis 251 of the upper cam member. The cross-sectional shape of the central cam member is perpendicular to a second longitudinal axis 253 of the central cam member. The cross-sectional shape of the lower cam member is also perpendicular to the first longitudinal axis 251.

The upper cam member 250 is fixedly coupled to the actuator 210. The central cam member 255 includes an outer radial surface 257 and extends through the first elongated slot 231 of end effector 230. The lower cam member 260 is rotatably secured to the housing 220. As shown in FIG. 17, the upper cam member 250 is mounted about an upper surface 256 of the central cam member 255. Similarly, the central cam member 255 is mounted about an upper surface 266 of the lower cam member 260.

In accordance with an aspect of the exemplary embodiment, the lower cam member 260 has a diameter substantially larger than a diameter of the central cam member 255. Similarly, the diameter of the central cam member 255 is substantially larger than a diameter of the upper cam member 250.

As shown in FIG. 17, the upper cam member 250 has first longitudinal axis 251 and the central cam member 255 has second longitudinal axis 253. It is to be understood that the first longitudinal axis 251 is offset from the second longitudinal axis 253. During operation, the actuator 210 and cam assembly 240 collectively pivotably rotate about the first longitudinal axis 251 of the upper cam member 250. In accordance with an aspect, the first longitudinal axis 251 and second longitudinal axis 253 are offset a distance Di of about 1 mm to about 2 mm. Preferably, the distance Di is about 1.52 mm, but can alternatively be less than or greater than 1.52 mm e.g., +/−0.001, 0.005, 0.010, 0.015 mm.

When the inserter assembly 200 is fully assembled, the lower cam member 260 is rotatably secured to a correspondingly shaped internal recess on the bottom 224 of the housing 220. The upper cam member 250 is fixedly coupled to the actuator 210 such that rotation of the actuator 210 results in corresponding rotation of the cam assembly 240 via the upper cam member 250. The central cam member 255 extends through the first elongated slot 231 of the end effector 230. The outer radial surface 257 of the central cam member 255 is configured to slidably travel along and abut the first inner perimeter 235, i.e., interior surface, of the first elongated slot 231. During rotation of the cam assembly 240, the lower cam member 260 is sized such that its upper surface 266 slidably engages a portion of the lower surface 239 of the end effector 230 to prevent the cam assembly from passing through the first elongated slot 231. In other words, it is to be understood that the upper surface 266 of the lower cam member 260 is sized such that it does not pass through the first elongated slot 231.

Referring now to FIGS. 10 and 18-20, the fulcrum 270 extends through the second elongated slot 232 of the end effector 230. The fulcrum 270 is shown as a pin and is preferably an elongated cylindrical member having a circular cross-sectional shape, however it can have any cross-sectional shape such as hexagonal, polygonal or any other shape suitable for its intended purpose. As shown, the cross-sectional shape is perpendicular to a longitudinal axis 275 of the fulcrum 270. It is to be understood that the fulcrum 270 can be formed with a plurality of segmented portions having different diameters. As shown in FIGS. 10 and 18, the fulcrum 270 has a first end 271 and a second end 272 opposite the first end. The fulcrum 270 further includes an outer radial surface 274. The first end 271 is mounted to a correspondingly shaped internal recess on the top 222 of the housing 220. The second end 272 is mounted to a correspondingly shaped internal recess on the bottom 224 of the housing 220. The fulcrum 270 further includes a collar portion 273 having a larger diameter and positioned between the first end 271 and the second end 272.

Figure 19:
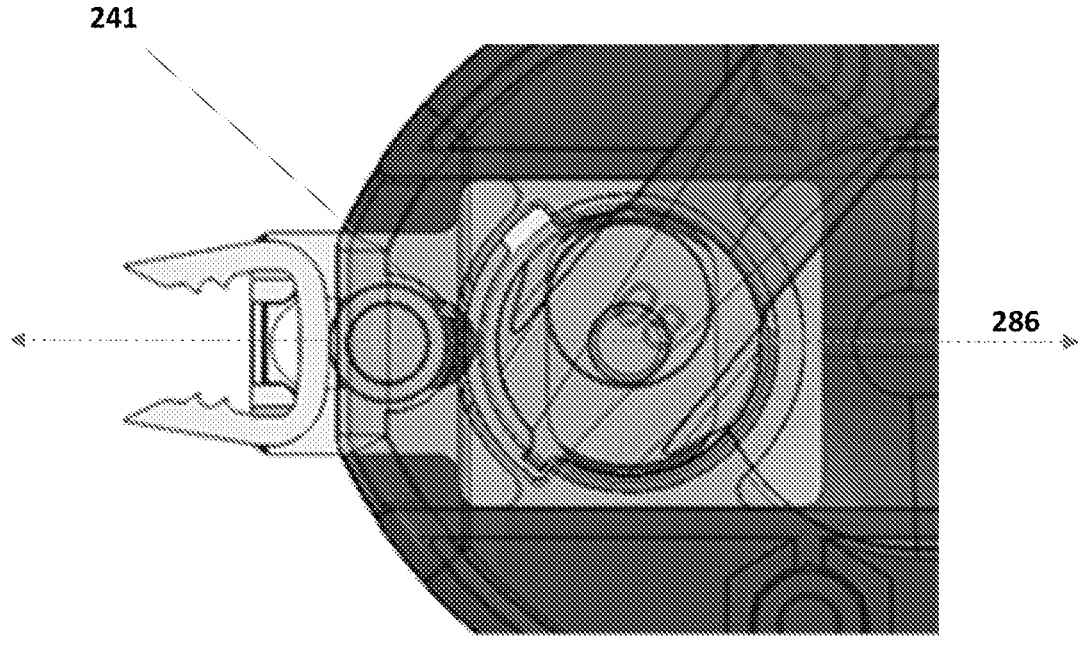
FIG. 19 is a partial top view of the inserter assembly of FIG. 9 in the first position with certain parts transparent for illustrative purposes.
Figure 20:
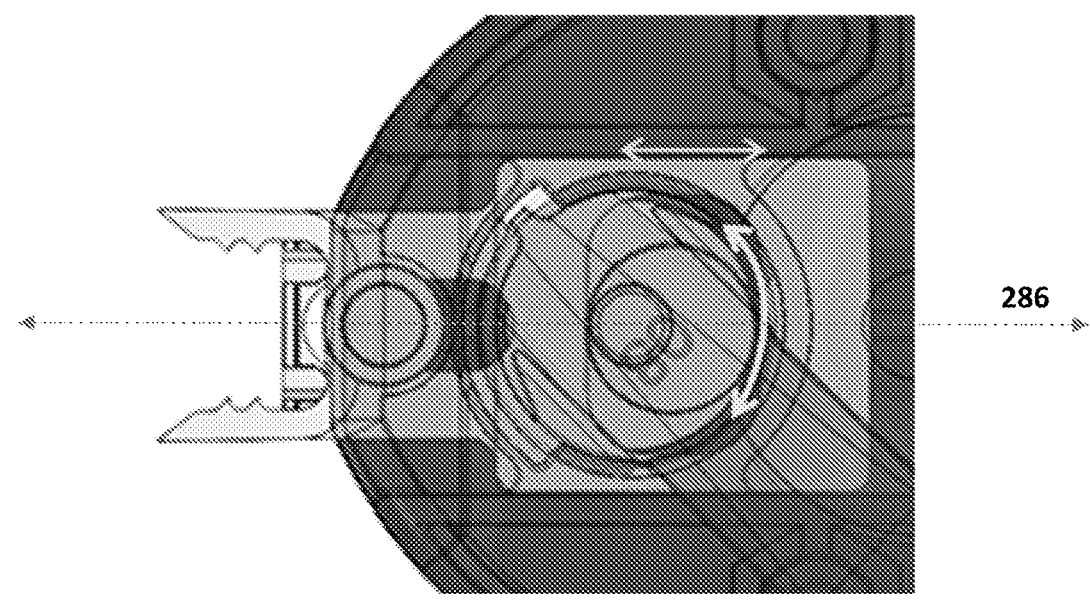
FIG. 20 is a partial top view of the inserter assembly of FIG. 9 in the second position with certain parts transparent for illustrative purposes.

In general, the fulcrum 270 extends through the second elongated slot 232. As shown in FIGS. 18-20, the fulcrum 270 slidably moves along the second elongated slot 232 as the end effector 230 moves from the first position to the second position. Specifically, the outer radial surface 274 of the fulcrum 270 is configured to slidably travel along the second inner perimeter 237 of the second elongated slot 232. The collar portion 273 is sized such that the fulcrum 270 does not pass through the second elongated slot 232. Accordingly, as the fulcrum 270 translates along the second elongated slot 232, the collar portion 273 engages or slides along a portion of the upper surface 233 of the end effector 230 to facilitate translational movement of the end effector from the first position to the second position.

The second elongated slot 232 is configured to limit movement of the end effector 230 between the first position and second position by creating a limited travel path for the fulcrum along the longitudinal axis 286 of the end effector. Specifically, when the end effector 230 is in the first position (FIG. 19), the collar portion 273 is configured to abut a radial stop 241 (FIG. 14) on the end effector 230 to prevent the end effector 230 from moving too far posteriorly. Similarly, when the end effector 230 is in the second position (FIG. 20), the collar portion 273 is configured to bias the staple 300 secured to the inserter assembly 200.

Figure 21:
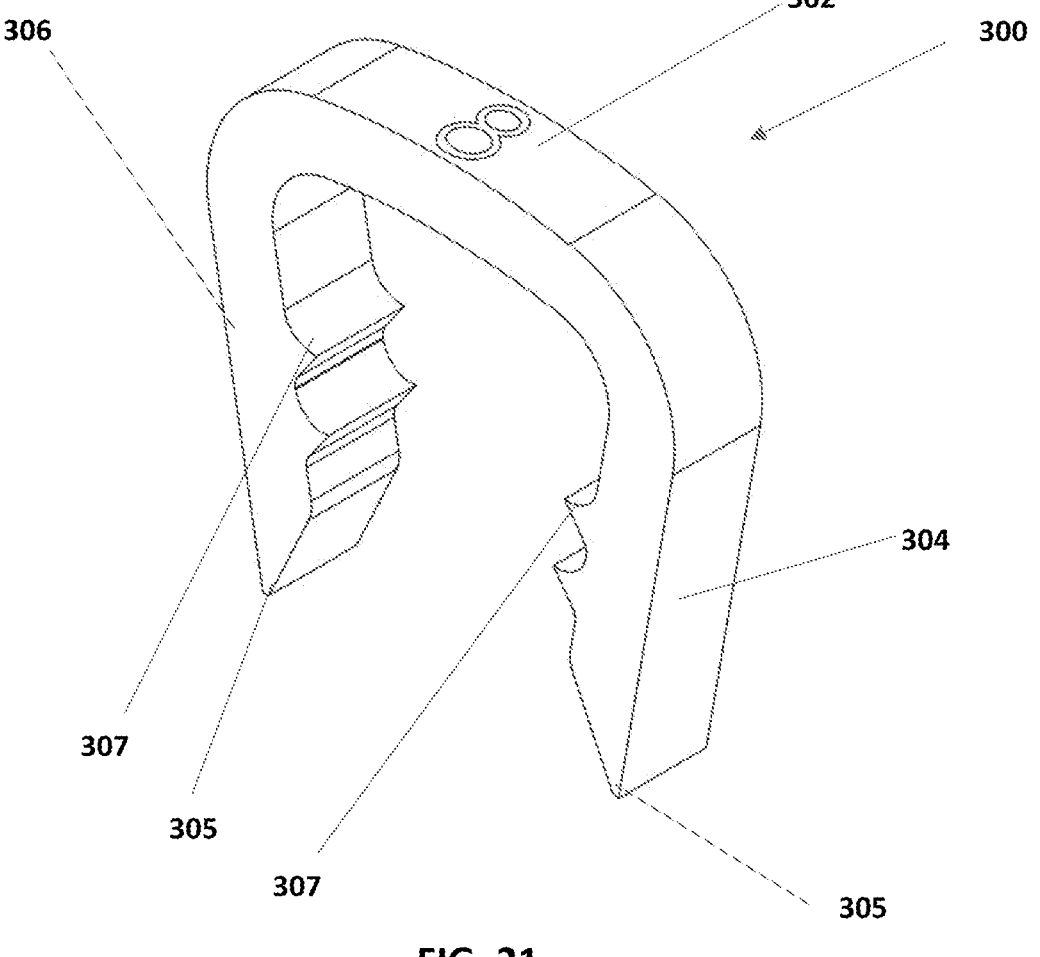
FIG. 21 is a perspective view of a staple applicable for use with the inserter assembly of FIG. 9.

Referring now to FIG. 21, there is shown staple 300 applicable for use with the inserter assembly 200 of the bone staple system. The staple 300 includes a bridge 302 and a pair of legs 304, 306 extending outwardly from the bridge. The legs 304, 306 each include a sharpened tip 305 about their anterior end to facilitate insertion of the staple 300 into respective holes drilled in adjacent bone segments. The bridge 302 is configured to connect respective posterior ends of the legs 304, 306.

The staple 300 can be formed from a surgical grade, bio-compatible metal, such as stainless steel, titanium alloy or any other suitable alloy suitable for its intended purpose. It is to be understood that the staple 300 of the present disclosure is preferably fabricated of a superelastic material which is sufficiently flexible to bend without breaking and is strong enough to provide a firm grip when positioned within pre-drilled holes in adjacent bone segments. In accordance with an aspect, the staple 300 is configured as a bone staple. Exemplary bone staples include, but are not limited to, mechanical staples, metal staples, staples that are bent by an instrument, or bendable staples, heat sensitive shape memory alloy staples or memory staples and mechanical elastic bone staples or elastic staples. For example, the staple can be made of a single piece of a shape memory alloy, such as, e.g., nitinol. As will be described below, the staple 300 is sufficiently flexible so that it is malleable between a first state (i.e., non-flexed state where the legs are biased inwardly) (see e.g., FIGS. 9, 11, and 19) and a second state (i.e., flexed state where the legs are biased away from each other relative to the first state) (see e.g., FIGS. 12 and 20).

The legs 304, 306 include texturing 307 that facilitate securing the legs 304, 306 in respective holes drilled in adjacent bone segments. The texturing 307 can include, but is not limited to, teeth, ridges, barbs, friction increasing elements, patterned divots, keels or gripping or purchasing projections. As shown in FIG. 21, the texturing 307 is preferably positioned on opposing inner surfaces of the legs 304, 306, such as those that face an opposing leg. It is to be understood that the texturing 307 may cover only a portion of the inner surface of the legs 304, 306, such as between 10-90%, and preferably between 25-50%. Alternatively, the legs 304, 306 can be coated with a titanium nitride (TiN) coating or aluminum nitride (AlTiN) coating to allow the legs to better engage the inner surfaces of the holes drilled in adjacent bone segments.

Alternatively, in another aspect, the legs 304, 306 can be formed from materials that contain osteoinductive, osteo-conductive, and/or germicidal surface properties (e.g., silicon nitride, zirconium oxide, or silver oxide) for promoting bone formation. Specifically, the osteoinductive and osteo-conductive properties of silicon nitride results in accelerated bone healing and bone fusion with surrounding bone.

The staple 300 can be of variable size or shape to accommodate different fixation procedures in the forefoot, midfoot, rear foot, ankle, and hand. For example, the length of the bridge 302 and the legs 304, 306 can be adjusted to accommodate the particular procedure or area of the body where adjacent bone segments or tissue are being fused or stapled together. In other words, it will be appreciated that the dimensions, gauge, and curvature of the bridge 302 as well as the legs 304, 306 are selected to allow the staple 300 to move to a flexed state that will deliver the desired compression requirements for proper bone healing where the staple is to be applied.

As discussed later with respect to the drill guide assembly 100, the drill head 120 will correspond to the desired staple width, length and diameter used by a surgeon for a procedure. For example, the length of bridge 302 can be of any size such as 10 mm, 11 mm, 12 mm, 15 mm, 18 mm, 20 mm, 25 mm, 30 mm, and the like to accommodate different fixation procedures for different bones within the body. In each case, it is to be understood that the length of bridge 302 represents the width of the staple 300 which is in turn reflected by the distance between a pair of guide members of the drill head 120 and the length between the projections 234, 236 on the end effector 230 upon which the staple is positioned and held.

Figure 11:
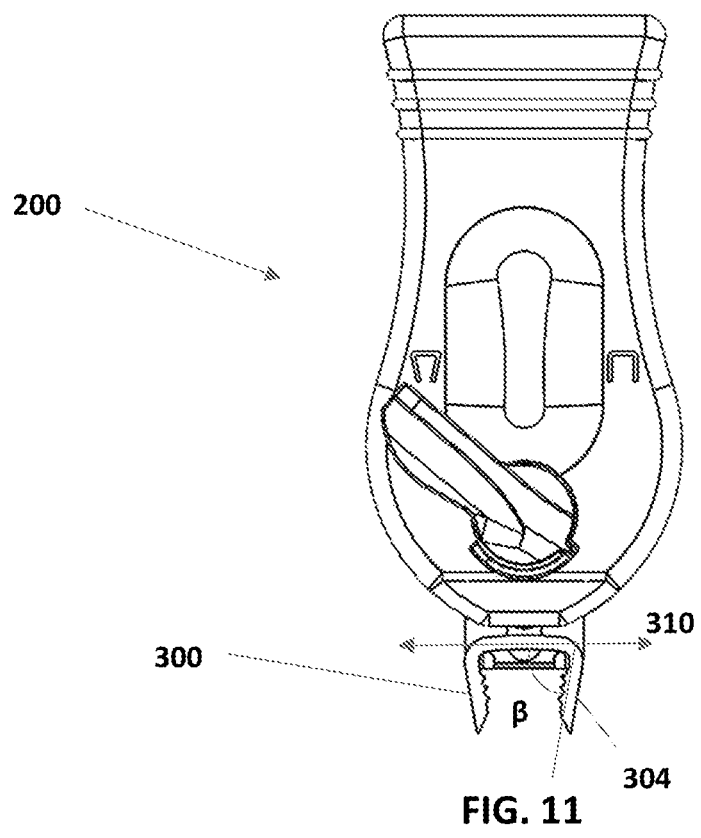
FIG. 11 is a top view of the inserter assembly of FIG. 9 in a first position.
Figure 12:
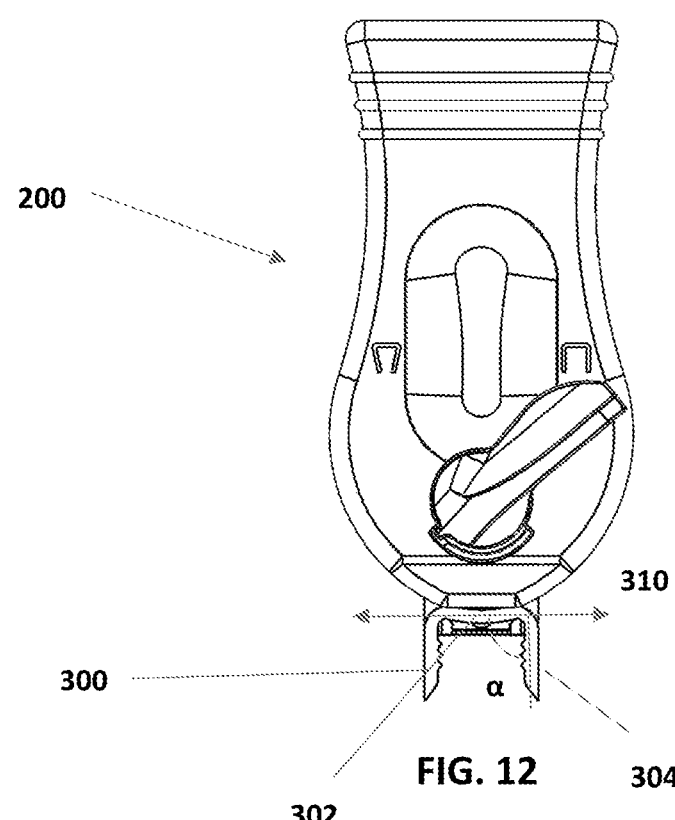
FIG. 12 is a top view of the inserter assembly of FIG. 9 in a second position.

As shown in FIGS. 9, 11 and 19, the staple 300 is non-flexed in the first state. That is, when in a non-flexed state, the respective legs 304, 306 of the staple are biased inwardly such that they naturally converge towards one another. Thereafter, as shown in FIGS. 12 and 20, the staple 300 is flexed in the second state. That is, when in a flexed state, the respective legs 304, 306 of the staple are mechanically deformed by a biasing force provided by the fulcrum 270 such that they extend at a substantially transverse direction to a longitudinal axis 310 of the bridge 302 to facilitate insertion of the staple into holes drilled in adjacent bone segments. As illustrated in FIG. 12, leg 304 and the longitudinal axis 310 of the bridge 302 define an angle α of about approximately 90 degrees. On the contrary, as illustrated in FIG. 11, the leg 304 and the longitudinal axis 310 of the bridge 302 define an angle β that is less than 90 degrees.

In sum, the staple 300 is configured to transition between the first state (i.e., converging state) where the legs converge (i.e., bias) inwardly toward each other and the second state (i.e., insertion state) where the legs bias outwardly or away from each other relative to the first state.

As described above, the inserter assembly 200 is configured to deliver staple 300 to the fixation site. Referring to FIGS. 1-5, the bone staple system includes drill guide assembly 100 to guide one or more instruments for preparing the fixation site for two adjacent bone segments. The drill guide assembly 100 is configured to facilitate forming holes in adjacent bone segments. As shown, the drill guide assembly includes a handle 110 and a drill head 120 that is removably coupled to the handle 110.

The drill guide assembly 100 can be manufactured from a number of materials that may be metallic or metallic alloys, such as nitinol, titanium alloys, non-titanium alloys, or polymeric materials, such as thermoplastic polymers or thermoset polymers, or ceramics. Exemplary polymeric materials may include polyetheretherketone (PEEK) or other biocompatible polymers. Ceramics may include, but are not limited to silicon nitride, zirconium oxide, silver oxide, and other suitable materials, both radiopaque and radiolucent.

The handle 110 can include a grip 111. Alternatively, the handle can be a base that can rest on or attach to a surface (not shown).

Figure 2:
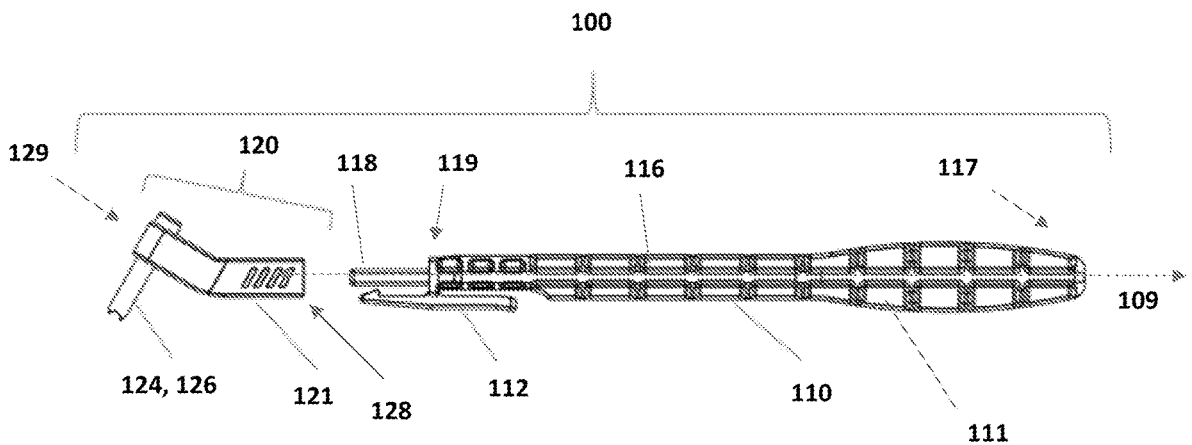
FIG. 2 is an exploded side view of the drill guide assembly of FIG. 1.

As shown in FIGS. 1 and 2, the handle 110 extends along a longitudinal axis 109 and includes a proximal end 117 and a distal end 119 opposite the proximal end 117 along the longitudinal axis 109, and a latching member 112 coupled to the distal end 119. The latching member 112 is configured to removably couple the drill head 120 to the handle 110, as described further below.

The handle 110 can further include an elongated member or shaft 116 that extends along the longitudinal axis 109. The shaft is preferably rigid and sized sufficiently to be gripped by a hand of a user. In one example, the shaft is a substantially cylindrical shaft having a substantially circular cross-sectional shape. As shown the cross-sectional shape is perpendicular to the longitudinal axis 109. The shaft can be other cross-sectional shapes as needed, e.g., such as hexagonal, polygonal or any other cross-sectional shape suitable to be ergonomically conformed to the hand of a user. In accordance with an aspect, the handle 110 may also include a plurality of handle segments with each having different cross-sectional dimensions. In addition, each handle segment could have different cross-sectional shapes. Generally, the handle 110 is illustrated as straight, but it may have a lordotic curve. Additionally, the handle 110 may have any desired length sufficient for its intended purpose.

The handle 110 includes grip 111 for facilitating a user's ability to grip and adjust the drill guide assembly 100. The grip 111 can be located along a portion of an entire length of the handle 110. Finally, the grip 111 may be configured as any suitable shape that may aid a user's ability to grip the drill guide assembly 100. For example, the grip may include depressions, grooves, finger slots, or any textured surface.

Figure 3:
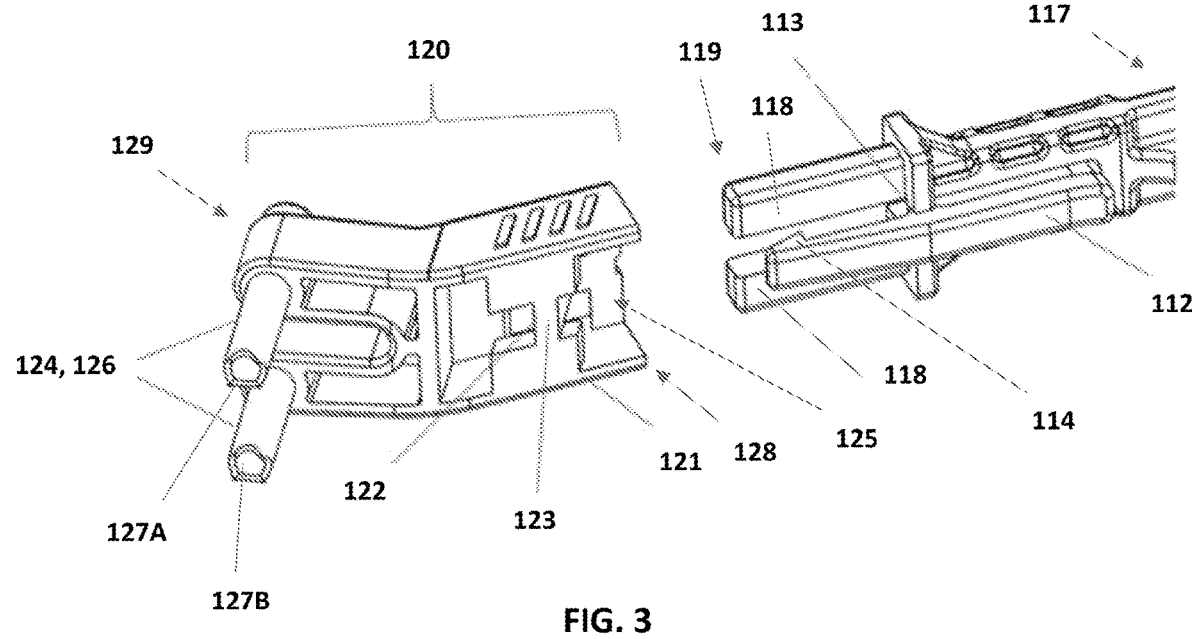
FIG. 3 is a partial bottom perspective view of the drill guide assembly of FIG. 1 in an unassembled position.
Figure 4:
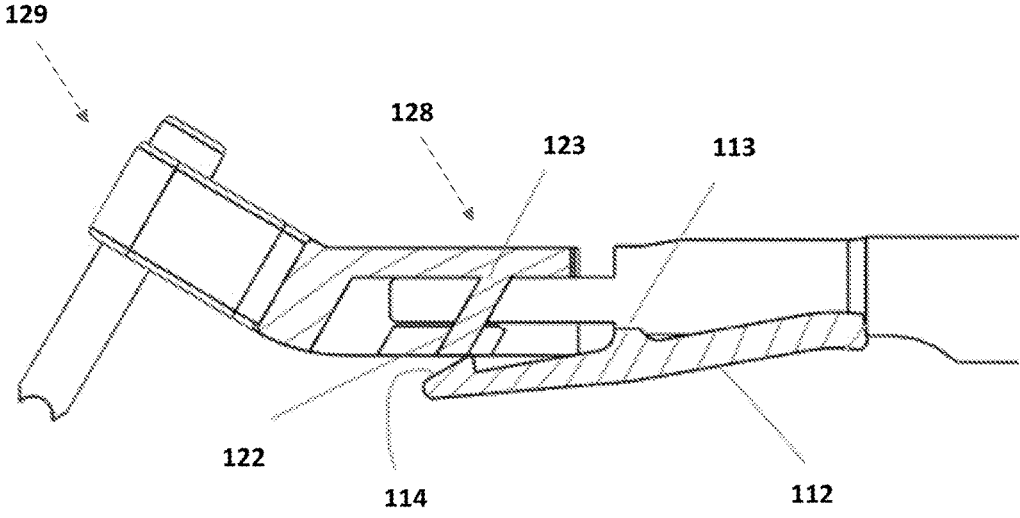
FIG. 4 is a partial side view of the drill guide assembly of FIG. 1 in a partially assembled position with certain parts shown in cross-section for illustrative purposes.
Figure 5:
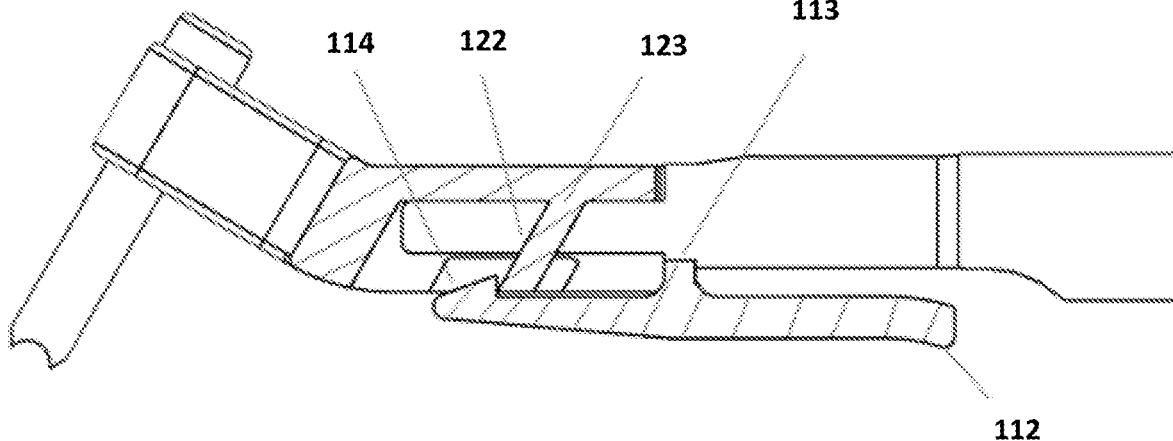
FIG. 5 is a partial side view of the drill guide assembly of FIG. 1 in an assembled position with certain parts shown in cross-section for illustrative purposes.
Figure 6A:
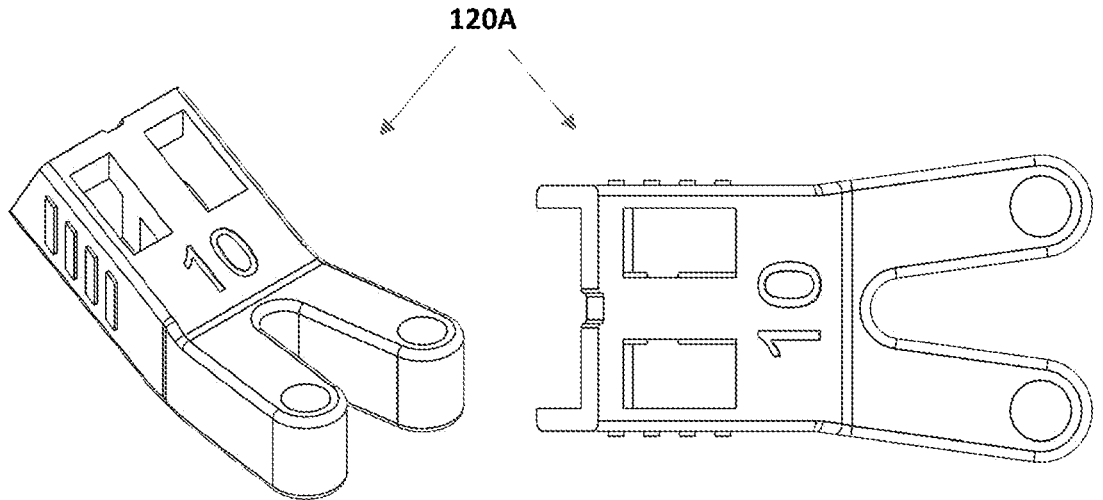
FIG. 6A is a pair of perspective views of a drill head applicable for use with the drill guide assembly of FIGS. 1-5.
Figure 6B:
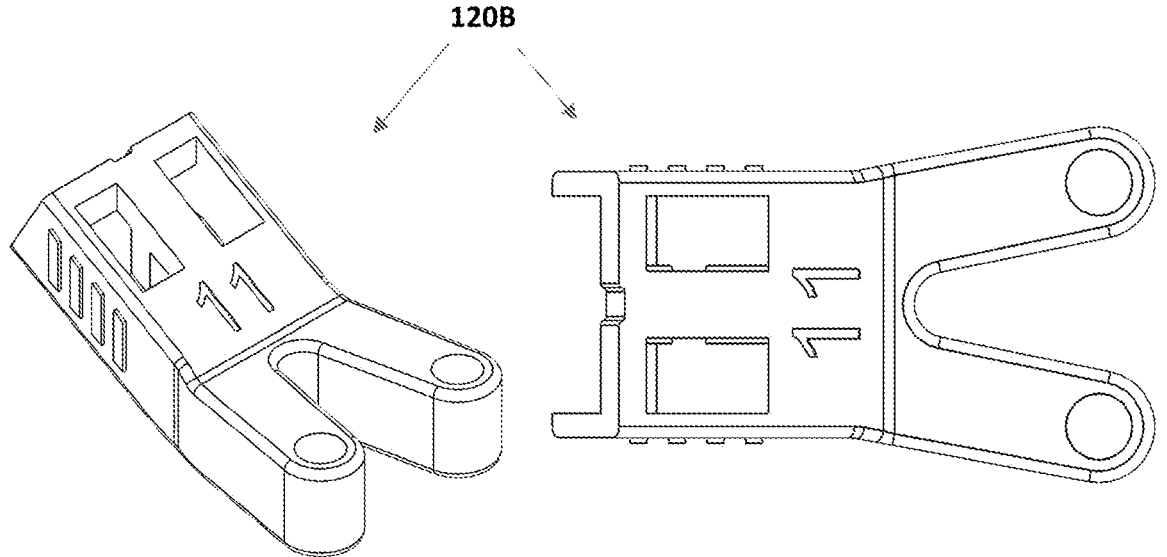
FIG. 6B is a pair of perspective views of another drill head applicable for use with the drill guide assembly of FIGS. 1-5.
Figure 6C:
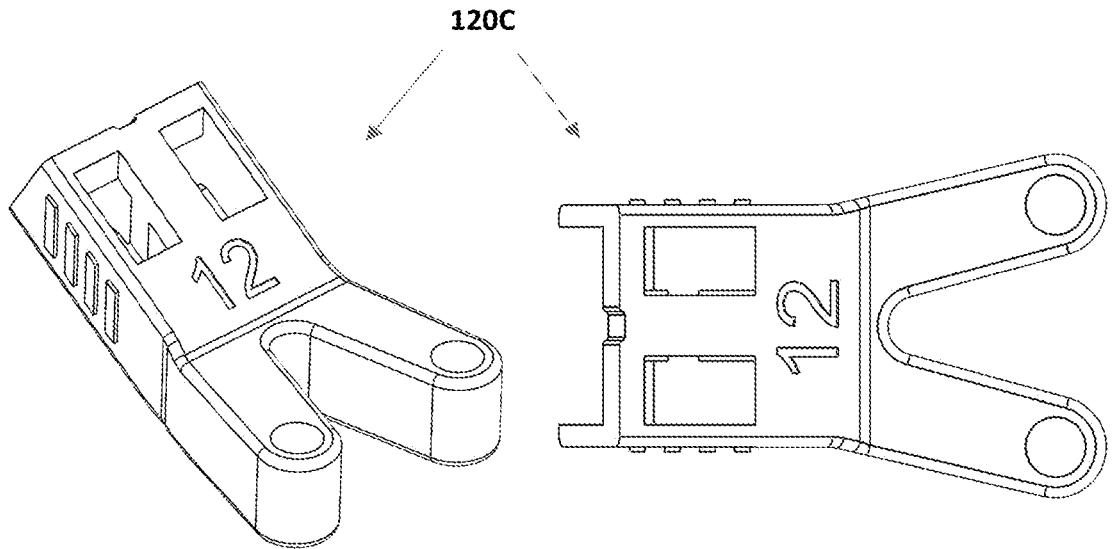
FIG. 6C is a pair of perspective views of another drill head applicable for use with the drill guide assembly of FIGS. 1-5.
Figure 6D:
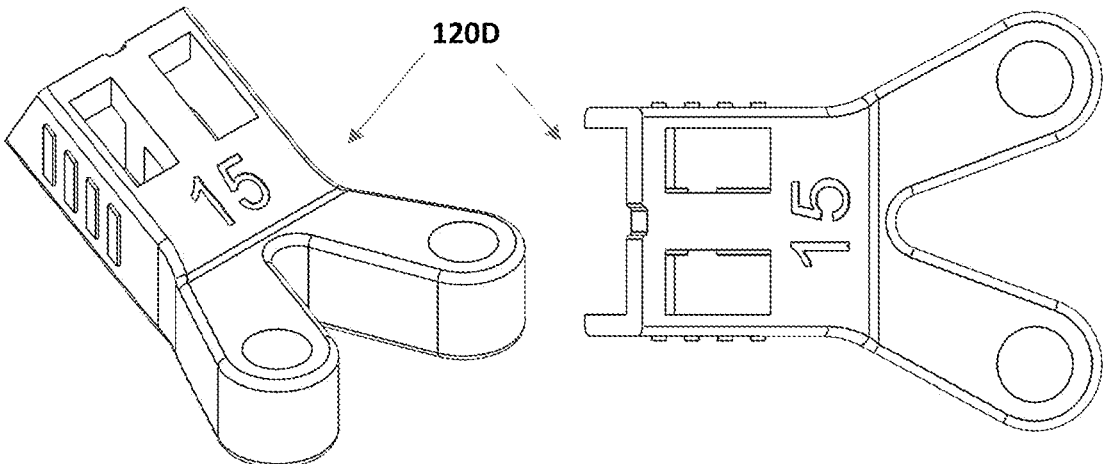
FIG. 6D is a pair of perspective views of another drill head applicable for use with the drill guide assembly of FIGS. 1-5.
Figure 6E:
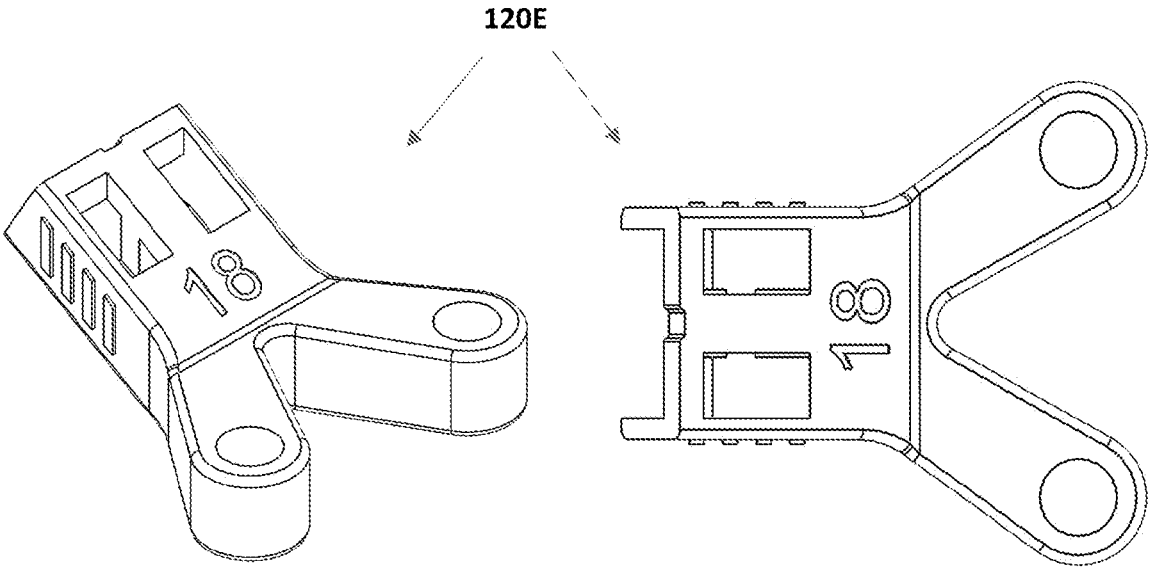
FIG. 6E is a pair of perspective views of another drill head applicable for use with the drill guide assembly of FIGS. 1-5.
Figure 6F:
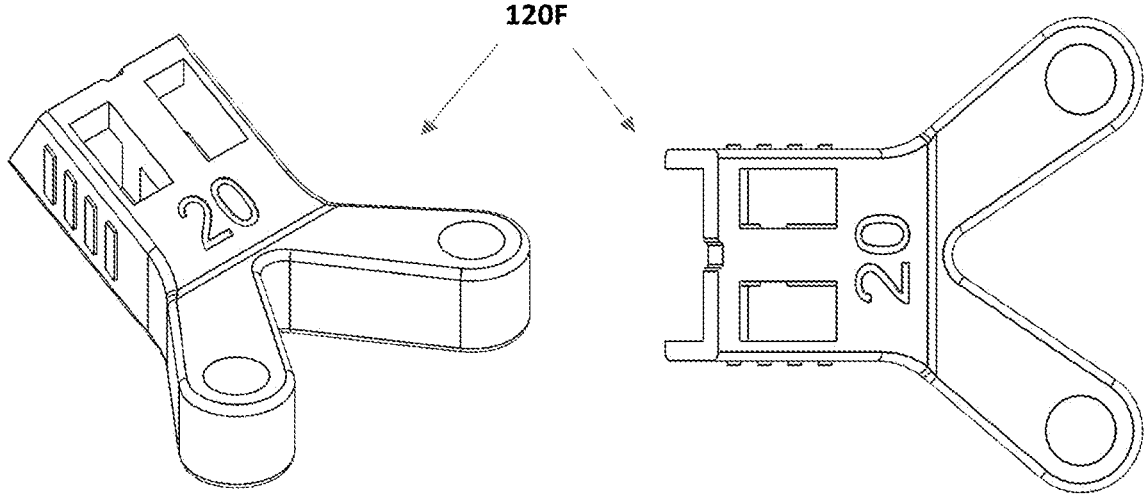
FIG. 6F is a pair of perspective views of another drill head applicable for use with the drill guide assembly of FIGS. 1-5.
Figure 6G:
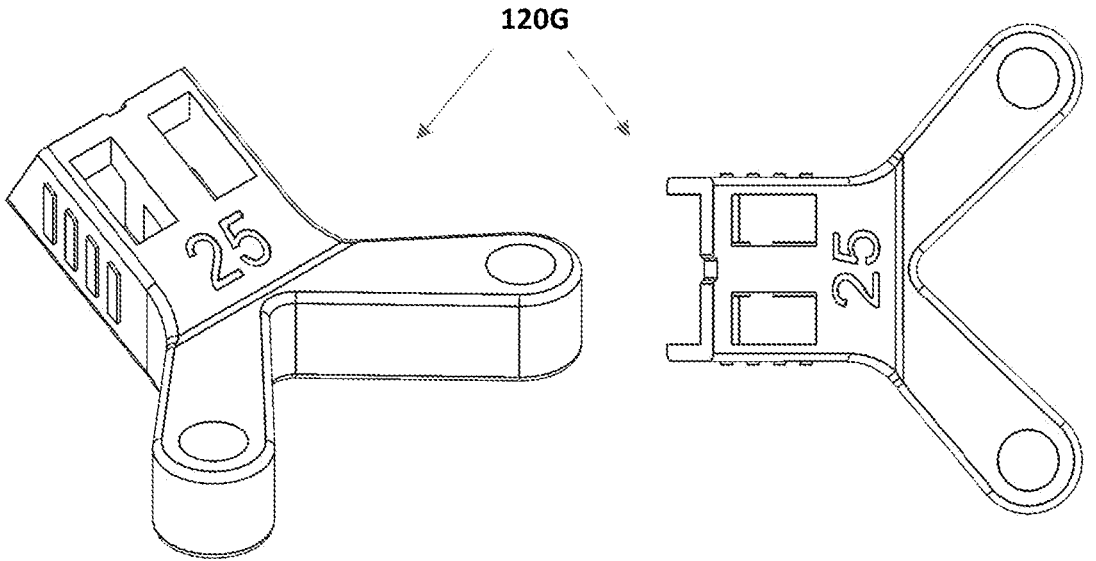
FIG. 6G is a pair of perspective views of another drill head applicable for use with the drill guide assembly of FIGS. 1-5.
Figure 6H:
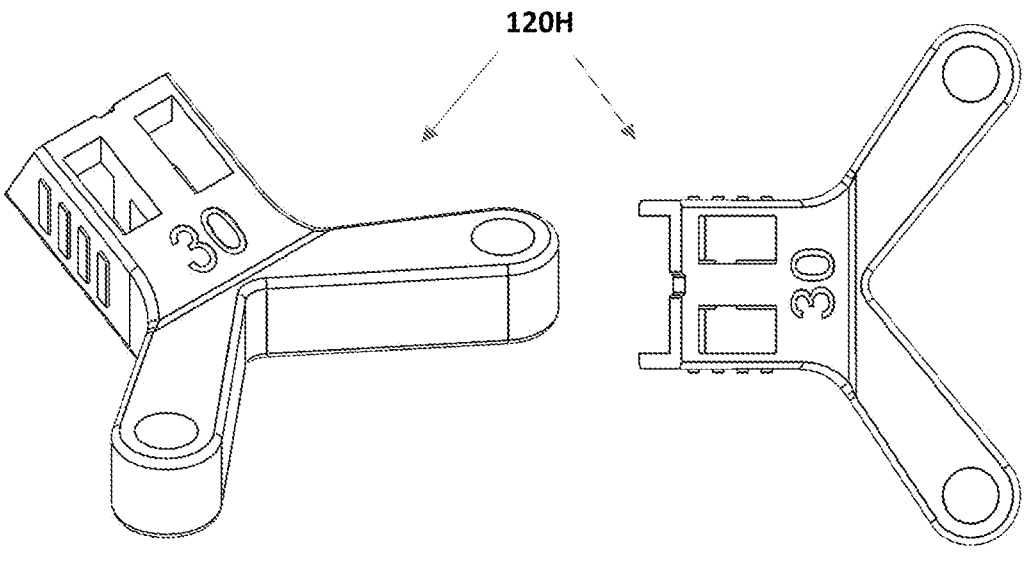
FIG. 6H is a pair of perspective views of another drill head applicable for use with the drill guide assembly of FIGS. 1-5.

As shown in FIGS. 3-5, the latching member 112 is configured to facilitate removable attachment of the drill head 120 to the handle 110. The latching member 112 may include a ramp 114 configured to engage a notch 122 on the drill head 120, a pair of legs 118 configured to be received within a recess of the drill head 120, and a thin section 113. The thin section 113 acts as a hinge between the handle 110 and the drill head 120. Configured this way, the latching member 112 has limited rotational movement to facilitate engagement of the ramp 114 with the notch 122 on the drill head.

Continuing with FIGS. 2-5, the drill head 120 includes a housing 121 having a first end 128 and a second end 129 that is opposite the first end. The first end 128 includes a recess 125 shaped to receive the legs 118 of the latching member 112. The second end 129 includes a pair of guide members 124, 126 configured to receive and guide a pair of drill bits toward the bone surface. The drill bits may be used to drill holes in the bone surface to receive the staple 300.

Figure 7:
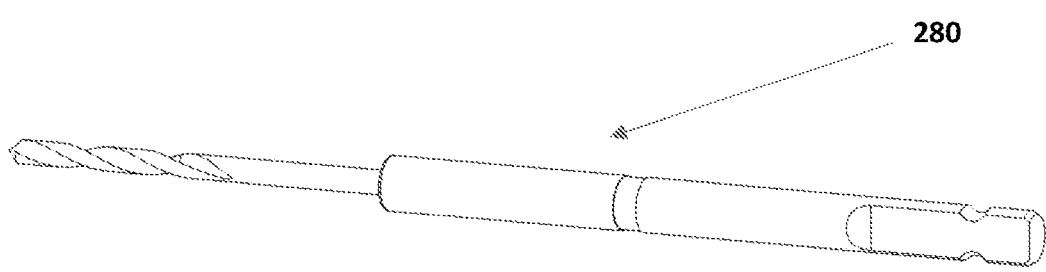
FIG. 7 is a perspective view of a drill bit applicable for use with the drill guide assembly of FIGS. 1-5.
Figure 8:
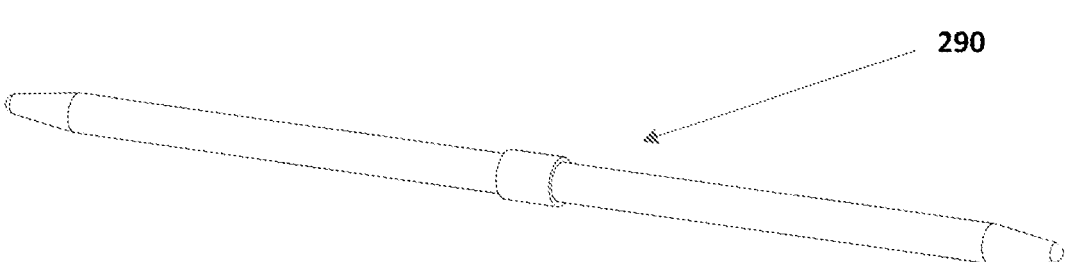
FIG. 8 is a perspective view of a locating pin applicable for use with the drill guide assembly of FIGS. 1-5.

As shown in FIG. 3, the guide members 124, 126 are configured as a pair of sleeves each having cannulations 127A, 127B that each extend along respective central axes. The guide members include an inner surface that defines the cannulations, each of which have a substantially circular cross section. However, the guide members and their cannulations have any cross-sectional shape that can receive drills, guide wires, etc., therein. For instance, the cannulations can have a hexagonal, polygonal or any other suitable cross-sectional shape. The cannulations 127A, 127B are configured to receive a drill bit 280 (FIG. 7). In addition, the cannulations 127A, 127B are configured to receive a locating pin 290 (FIG. 8) to facilitate proper placement of the drill guide assembly during an operation.

As best shown in FIGS. 3 and 4, the first end 128 of the housing 121 further includes notch 122 for engaging the latching member 112. Specifically, a wall 123 of the notch 122 engages the ramp 114 of the latching member 112 to releasably secure the handle 110 to the drill head 120.

The drill head 120 is removably coupled to the handle 110 such that the drill head 120 can be easily removed from the handle 110 as required. This allows the surgeon to select the appropriate drill head 120 based on the fracture and anatomy at the fixation site.

Referring to FIGS. 6A-6H, there are shown a variety of different interchangeable drill heads 120A-H with varying size and dimensions for use with the drill guide assembly of the present disclosure. To assemble the drill guide assembly 100, a user pushes the drill head 120 onto the distal end 119 of the handle 110 such that the legs 118 are received within recess 125 of the housing 121. As the user pushes the drill head 120 and handle 110 together, the ramp 114 of the latching member 112 rides over wall 123 of the notch 122 such that the ramp is secured within a slot of the drill head 120.

In order to release drill head 120 from handle 110, the user pushes a proximal end of the latching member 112 causing the ramp 114 to rise over wall 123 of the notch 122 so that the user can simply detach the drill head from the handle.

In operation, upon identification of two adjacent bone segments to be stapled, a user determines the proper drill head to use based on a desired staple width, length, and diameter. The identified drill head is coupled to the handle of the drill guide assembly. Thereafter, the assembled drill guide assembly is positioned on the pre-determined bone surfaces where a staple is to be implanted. In order to facilitate positioning of the drill guide assembly, the user may use the locating pin 290. Once the drill guide assembly is positioned, the user uses correspondingly sized drill bit 280 to drill holes into the respective bone surfaces for insertion of the staple. Thereafter, the inserter assembly 200 is used to deliver the staple 300 to the holes drilled by the drill guide assembly 100 at the fixation site for securing adjacent bone segments.

In accordance with an aspect of the present disclosure, the staple 300 is loaded onto the end effector 230 of inserter assembly 200 when the staple is in the non-flexed state (i.e., first state). Specifically, the end effector 230 includes projections 234, 236 to facilitate adjustably securing the staple 300 to the inserter assembly 200. When the staple 300 is mounted to the engagement end 281 of the end effector 230, the projections 234, 236 provide a biasing force against respective inner surfaces of the staple to secure the staple in place to the inserter assembly 200. In accordance with another aspect, the staple 300 can be supplied pre-loaded on the inserter assembly or multiple staples can be pre-loaded onto the inserter assembly by a user.

Once the staple 300 is adjustably secured to the inserter assembly via the projections 234, 236 for insertion into the holes drilled in adjacent bone segments, the actuator 210 is then rotated by a user. As a result, the actuator 210 and the cam assembly 240 collectively rotate about the first longitudinal axis 251 of the upper cam member 250 i.e., the pivot point. As shown in FIGS. 18-20, rotary motion of the actuator 210 and cam assembly 240 is converted into linear movement of the end effector 230. That is, as actuator 210 is rotated, the central cam member 255 rotatably moves along the first elongated slot 231 of the end effector 230.

Specifically, the outer radial surface 257 of the central cam member 255 slidably travels along and biases the first inner perimeter 235 of the first elongated slot 231. As the central cam member 255 biases the first inner perimeter 235, the end effector 230 translates laterally and outwardly from the first position (FIG. 19) to the second position (FIG. 20). That is, the second position is anteriorly spaced from the first position. When the end effector 230 translates laterally, the fulcrum 270 correspondingly slidably moves along the second elongated slot 232. As a result, collar portion 273 of the fulcrum 270 biases the bridge 302 of the staple 300 such that the legs 304, 306 move from the non-flexed state (i.e., first state) to the flexed state (i.e., second state) for facilitating insertion of the staple into the holes drilled in respective bone segments. In other words, the substantially annular central cam member 255 is adapted to transmit torque from rotation of the actuator 210 and cam assembly 240 extending through the end effector 230 into linear movement of the end effector 230 along the longitudinal axis of the housing 220 such that fulcrum 270 provides a biasing force to deform the staple 300 into the flexed state.

Once the staple 300 is in the flexed state, it is implanted into the holes drilled in respective bone segments. Once the staple 300 is fully implanted, the inserter assembly 200 is removed. Thereafter, a tamp may be used to mallet the staple 300 into the holes drilled in the adjacent bone segments until it is fully seated. Upon removal of the inserter assembly 200, the staple 300 returns to its natural non-flexed state where the legs 304, 306 converge inwardly toward one another. As a result, a compression force is applied to the fracture to secure the adjacent bone segments together to facilitate healing.

Embodiments of the present disclosure will now be further described with respect to exemplary methods that utilize the bone staple system described herein. For example, the bone staple system may be used in a particular method for anchoring a staple to a fixation site of two or more bone segments. The method includes positioning a hub (i.e., end effector) of an inserter assembly toward the fixation site, wherein the hub carries a staple having a pair of legs that are biased inwardly in a converging state. The method also includes advancing the hub that carries the staple having the pair of legs in a proximal direction toward a proximal end of the inserter assembly so that a bridge of the staple abuts a fulcrum (i.e., pin) mounted to a distal end of the inserter assembly, thereby causing the pair of legs of the staple to bias outwardly from the converging state, where the pair of legs are biased toward each other, to an insertion state out of the converging state. The method also includes inserting the pair of legs into two or more bone segments so that the bridge of the staple traverses the fixation site while the staple is in the insertion state and advancing the hub in a distal direction that is opposite the proximal direction, thereby causing the pair of legs to converge inwardly toward the converging state in order to anchor the staple at the fixation site.

Implementations may include one or more of the following features or steps. The method may include, after advancing the hub in the distal direction, releasing the staple from the hub of the inserter assembly. The staple is secured to the hub of the inserter assembly via a plurality of projections. The hub is moveable along a longitudinal axis relative to the inserter assembly between a first position and a second position. The method may include, wherein advancing the hub in the proximal direction causes the pin to apply a force to the bridge of the staple in order to bias the pair of legs outwardly into the insertion state. The method may include, wherein advancing the hub in the proximal direction includes rotating an actuator coupled to the hub to cause the hub to translate along the longitudinal axis relative to the inserter assembly between a first position, where the staple is in the converging state, and a second position, where the staple is in the insertion state. The method may further include, wherein rotation of the actuator about a rotation axis that is perpendicular to the longitudinal axis causes the hub to move in the proximal direction along the longitudinal axis.

The method may include, wherein advancing the hub in the proximal direction toward the proximal end of the inserter assembly includes actuation of a cam assembly coupled to the hub to cause the hub to translate in the proximal direction toward the pin. The method may further include, before positioning the hub of the inserter assembly toward the fixation site, positioning a staple on the hub.

Another general example includes a method for anchoring a staple to a fixation site of two or more bone segments. The method includes positioning an end effector of an inserter assembly in alignment with the fixation site, wherein the end effector carries a staple having a bridge and a pair of legs in a converging state where the legs converge inwardly toward each other. The method also includes advancing the end effector in a proximal direction toward a proximal end of a housing of the inserter assembly so that the bridge of the staple abuts a pin mounted within the housing, so as to apply a force to the bridge that biases the pair of legs of the staple outwardly into an insertion state. The method further includes implanting the pair of legs, when in the insertion state, into the fixation site, and retracting the end effector in a distal direction that is opposite the proximal direction, so as to cause the pair of legs to converge inwardly to secure the staple at the fixation site.

Implementations may include one or more of the following features or steps. The method may include, wherein advancing the end effector in the proximal direction toward the proximal end of the inserter assembly includes actuation of a cam assembly coupled to the end effector, which causes the end effector to translate in the proximal direction toward the pin. The method may further include, before positioning the end effector of the inserter assembly in alignment with the fixation site, positioning a staple on the end effector.

Wherever possible, the same or like reference numbers are used throughout the drawings to refer to the same or like features. It should be noted that the drawings are in simplified schematic form and are not drawn to precise scale. Certain terminology is used in the description is for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the present disclosure in any manner not explicitly set forth. Additionally, the term "a," as used in the specification, means "at least one." The terminology includes the words above specifically mentioned, derivatives thereof, and words of similar import.

"Substantially" as used herein shall mean considerable in extent, largely but not wholly that which is specified, or an appropriate variation therefrom as is acceptable within the field of art. "Exemplary" as used herein shall mean serving as an example.

Furthermore, the described features, advantages and characteristics of exemplary embodiments may be combined in any suitable manner in one or more embodiments. One skilled in the art will recognize, in light of the description herein, that the exemplary embodiments can be practiced without one or more of the specific features or advantages of a particular embodiment. In other instances, additional features and advantages may be recognized in certain embodiments that may not be present in all embodiments of the present disclosure.

While the disclosure is described herein, using a limited number of embodiments, these specific embodiments are not intended to limit the scope of the disclosure as otherwise described and claimed herein. The precise arrangement of various elements and order of the steps of articles and methods described herein are not to be considered limiting. For instance, although the steps of the methods are described with reference to sequential series of reference signs and progression of the blocks in the figures, the method can be implemented in an order as desired.

The invention claimed is:
1. A bone staple system, comprising:
an inserter assembly configured to deliver a staple into a fixation site, the inserter assembly having:
a housing including a leading end, a trailing end opposite the leading end along a longitudinal axis;
an end effector that is moveable along the longitudinal axis relative to the housing between a first position and a second position;
a fulcrum fixed to the housing and that engages the end effector, wherein the fulcrum and the end effector are configured to hold the staple;
a cam assembly coupled to the end effector, the cam assembly including cam members fixedly connected to one another, wherein at least two cam members are positioned eccentrically; and
an actuator coupled to the cam assembly;
wherein actuation of the actuator moves the end effector between the first position and the second position.
2. The bone staple system of claim 1, further comprising a drill guide assembly configured to guide one or more instruments for preparation of a fixation site for two adjacent bone segments, the drill guide assembly having a handle, and a plurality of interchangeable drill heads, each of which are configured to be removably coupled to the handle.
3. The bone staple system of claim 2, wherein the handle includes a latching member configured to removably couple the handle to the drill head.
4. The bone staple system of claim 3, wherein the latching member is configured to engage a notch on the drill head.
5. The bone staple system of claim 2, wherein the drill head includes a pair of guide members configured to receive a drill bit for drilling a pair of holes.
6. The bone staple system of claim 2, wherein the drill head includes a pair of guide members configured to receive a locating pin.
7. The bone staple system of claim 2, wherein the drill head includes a pair of guide members arranged a distance apart, the distance being based on a size of a staple.
8. The bone staple system of claim 1, further comprising a staple having a bridge and a pair of legs extending from the bridge.
9. The bone staple system of claim 8, wherein the staple is configured to transition between a first state where the legs are biased inwardly toward each other and a second state where the legs are biased away from each other relative to the first state.
10. The bone staple system of claim 8, wherein the fulcrum is configured to provide a biasing force capable of causing the staple to move to a flexed state when the end effector is in the second position.
11. The bone staple system of claim 8, wherein the staple is adjustably secured to the inserter assembly via a pair of projections.
12. The bone staple system of claim 1, wherein the actuator is rotatable about a rotation axis that is perpendicular to the longitudinal axis, wherein rotation of the actuator about the rotation axis causes the end effector to move in a proximal direction along the longitudinal axis toward the trailing end of the housing.
13. The bone staple system of claim 12, wherein rotation of the actuator causes actuation of the cam assembly coupled to the end effector.
14. An inserter assembly configured to deliver a staple into a fixation site, the inserter assembly comprising:
a housing including a leading end, a trailing end opposite the leading end along a longitudinal axis;
an end effector that is moveable along the longitudinal axis relative to the housing between a first position and a second position;
a pin fixed to the housing and that engages the end effector, wherein the pin and the end effector are configured to secure the staple;
a cam assembly coupled to the end effector, the cam assembly including cam members fixedly connected to one another, wherein at least two cam members are positioned eccentrically;
an actuator coupled to the cam assembly; and
wherein actuation of the actuator moves the end effector between the first position and the second position.

15. The inserter assembly of claim 14, the cam members including:

an upper cam member fixedly coupled to the actuator, a central cam member extending through the end effector, and a lower cam member rotatably secured to the housing.

16. The inserter assembly of claim 15, wherein the central cam member extends through a first elongated slot of the end effector.

17. The inserter assembly of claim 15, wherein the upper cam member has a first longitudinal axis offset from a second longitudinal axis of the central cam member.

18. The inserter assembly of claim 15, wherein the actuator and the cam assembly pivotably rotate about a first longitudinal axis of the upper cam member.

19. The inserter assembly of claim 18, wherein rotation of the actuator about the first longitudinal axis causes the central cam member to rotatably move along a first elongated slot of the end effector.

20. The inserter assembly of claim 19, wherein the central cam member is configured to bias an inner perimeter of the first elongated slot causing the end effector to translate laterally and outwardly from the first position to the second position.

21. The inserter assembly of claim 14, wherein the end effector is movable relative to the housing between the first position and the second position.

22. The inserter assembly of claim 21, wherein the second position is anteriorly spaced from the first position.

23. The inserter assembly of claim 14, wherein the pin extends through a second elongated slot of the end effector spaced from a first elongated slot of the end effector.

24. The inserter assembly of claim 23, wherein the pin slidably moves along the second elongated slot as the end effector moves from the first position to the second position.

25. The inserter assembly of claim 24, wherein the pin is configured to bias the staple secured to the inserter assembly when the end effector is in the second position.

26. The inserter assembly of claim 14, wherein the end effector includes a pair of projections for adjustably securing the staple to the inserter assembly.

27. The inserter assembly of claim 14, wherein the actuator is rotatable about a rotation axis that is perpendicular to the longitudinal axis, wherein rotation of the actuator about the rotation axis causes the end effector to move in a proximal direction along the longitudinal axis toward the trailing end of the housing.

28. The inserter assembly of claim 27, wherein rotation of the actuator causes actuation of the cam assembly coupled to the end effector.

29. A bone staple system, comprising:

an inserter assembly configured to deliver a staple into a fixation site, the inserter assembly having:

a housing including a leading end, a trailing end opposite the leading end along a longitudinal axis;

an end effector that is moveable along the longitudinal axis relative to the housing between a first position and a second position;

a fulcrum fixed to the housing and that engages the end effector, wherein the fulcrum and the end effector are configured to hold the staple;

a cam assembly coupled to the end effector; and an actuator coupled to the cam assembly;

wherein actuation of the actuator moves the end effector between the first position and the second position, wherein the end effector in the second position is configured to flex the staple such that a distance between legs of the staple remains constant for insertion.

* * * * *